(12) United States Patent
Puel et al.

(10) Patent No.: US 7,589,110 B2
(45) Date of Patent: Sep. 15, 2009

(54) DELIVERY OF MODULATORS OF GLUTAMATE-MEDIATED NEUROTRANSMISSION TO THE INNER EAR

(75) Inventors: Jean-Luc Puel, Cournonterral (FR); Remy Pujol, Florensac (FR); Yves Christen, Paris (FR)

(73) Assignees: Durect Corporation, Cupertino, CA (US); Inserm, Paris (FR)

( * ) Notice: Subject to any disclaimer, the term of this patent is extended or adjusted under 35 U.S.C. 154(b) by 645 days.

(21) Appl. No.: 10/525,624

(22) PCT Filed: Sep. 6, 2002

(86) PCT No.: PCT/US02/28519

§ 371 (c)(1), (2), (4) Date: Nov. 3, 2005

(87) PCT Pub. No.: WO2004/022069

PCT Pub. Date: Mar. 18, 2004

(65) Prior Publication Data

US 2007/0015727 A1      Jan. 18, 2007

(51) Int. Cl.
*A61K 31/7072* (2006.01)
(52) U.S. Cl. ...................................................... 514/326
(58) Field of Classification Search .................. 514/326
See application file for complete search history.

(56) References Cited

U.S. PATENT DOCUMENTS

| 5,039,528 A * | 8/1991 | Olney ........................ 424/451 |
| 6,265,379 B1 * | 7/2001 | Donovan ...................... 514/14 |
| 2004/0102525 A1 * | 5/2004 | Kozachuk ................... 514/662 |

OTHER PUBLICATIONS

Liu et al. Toxicol. Appl. Pharmacol., 1995; 132: 196-202.*
Laplanche et al. Neuroscience Lett. 2000; 289: 49-52.*

* cited by examiner

*Primary Examiner*—Kamal A Saeed
*Assistant Examiner*—Valerie Rodriguez-Garcia
(74) *Attorney, Agent, or Firm*—Thomas P. McCracken

(57) ABSTRACT

The invention features methods and devices for local delivery of agents that modify glutamate-mediated neurotransmission to the inner ear for treatment of inner ear disorders caused by glutamate-induced hearing loss and/or tinnitus.

5 Claims, 7 Drawing Sheets

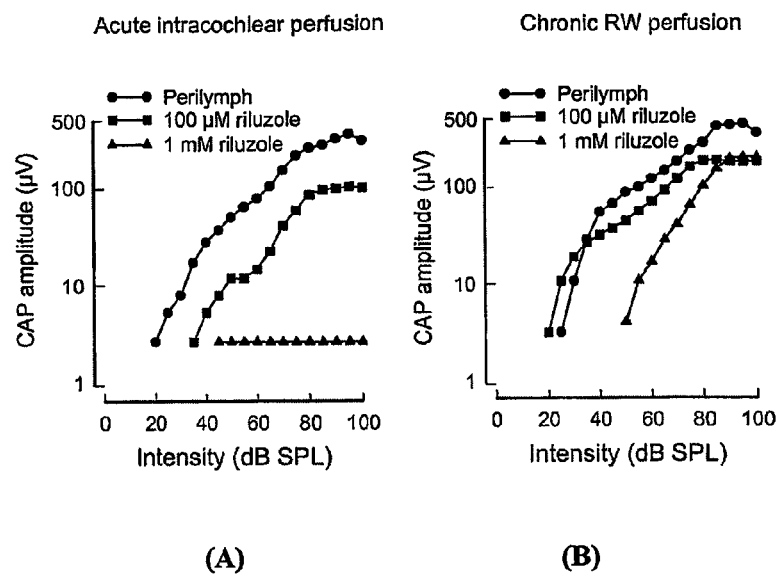

Example 1: Comparative effect of acute intracochlear perfusion and chronic round window perfusion. These graphs represent the mean amplitude of the CAP as the function of the intensity of 8kHz tone burst stimulation. Mean threshold has been calculated from 5 different animals. Note that both acute intracochlear and chronic round window application of riluzole reduce the CAP amplitude in a dose-dependent manner. However, the effect was 10 times less potent when the drug was applied onto the round window.

FIG. 2

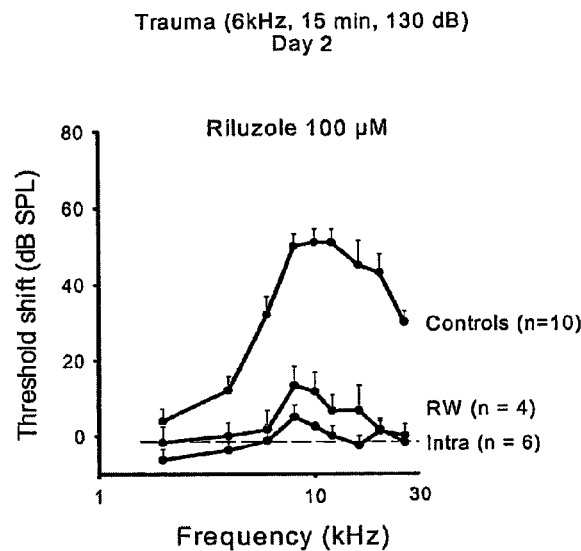

Example 2: Protective effect of riluzole on intense noise induced acoustic trauma.
CAP audiograms (threshold shifts as the function of tone frequency) were measured 2 days after 30 minutes of continuous sound exposure. Threshold shift was calculated as the difference in the recording before and 2 days after 6kHz continuous tone exposure. Shown are threshold shift recorded after 120 dB SPL exposure during 30 minutes in presence of artificial perilymph (red curve, control). Note the clear protection of 100 μM riluzole when either applied directly into the cochlea (blue curve, intra) or onto the round window (green curve, RW). "n" is the number of tested animals

FIG. 3

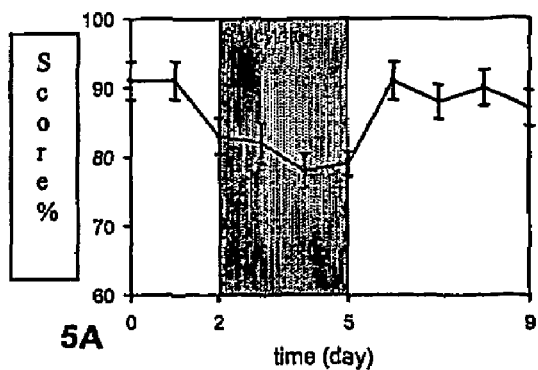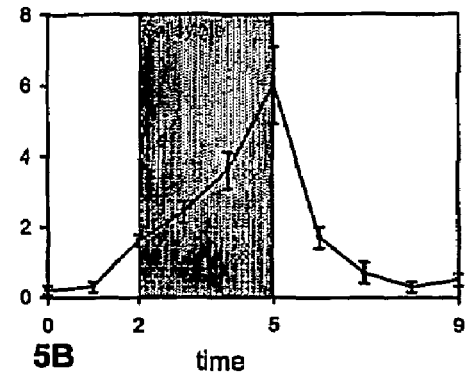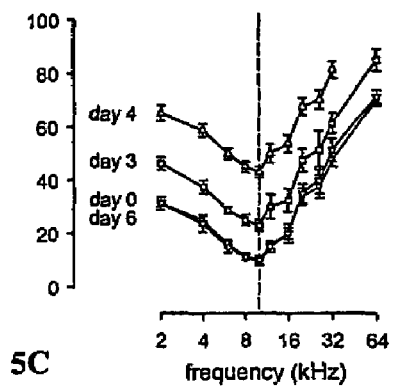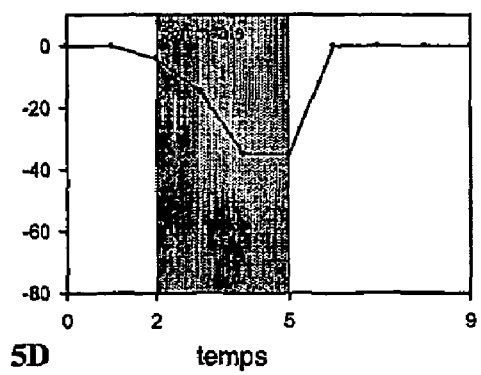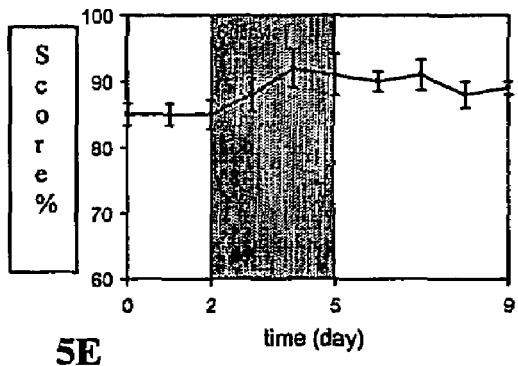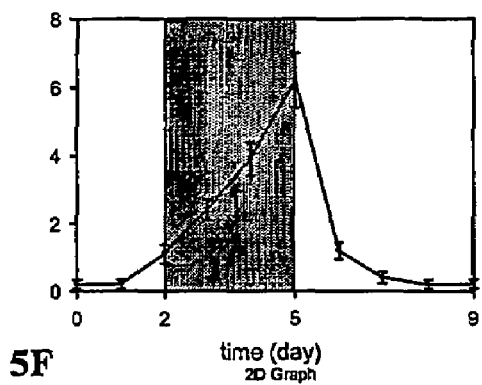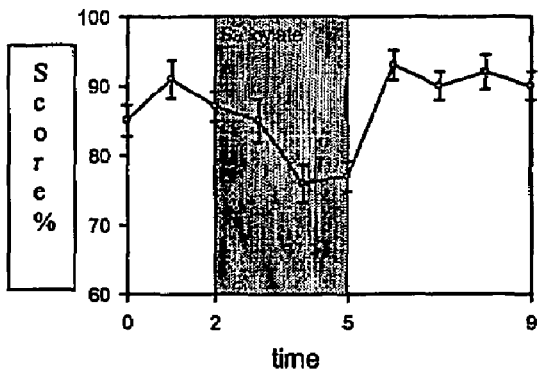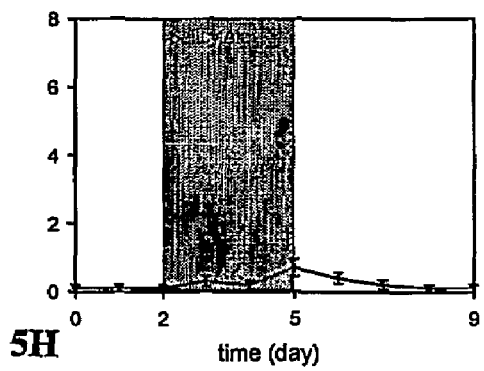
FIGS. 5A-H

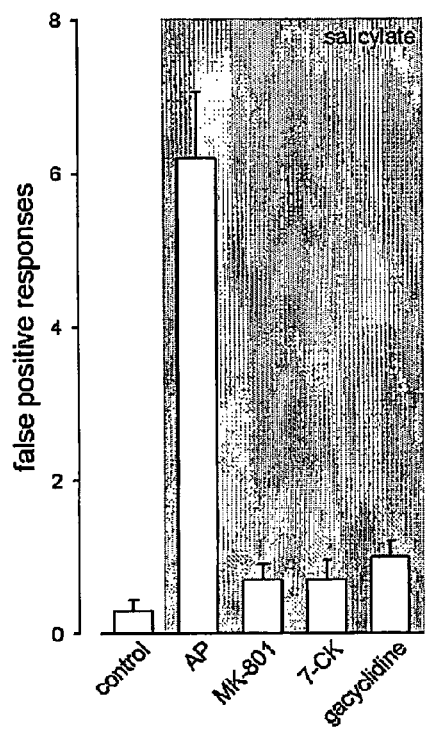

Fig 6. Comparative effects on NMDA antagonists on salicylate-induced tinnitus. Shown are the number of false positive responses measured at the end salicylate treatment (day 4) in animals with gelfoams bathed with artificial perilymph alone (AP, n=10) alone or MK-801 (10 μM, n=10), 7-chlorokynurenate (7-CK, 50 μM, n=10), or gacyclidine (50 μM, n=10). When compared with AP alone, local application of MK-801, 7-CK, or gacyclidine drastically reduced the occurrence of the false positive responses.

DELIVERY OF MODULATORS OF GLUTAMATE-MEDIATED NEUROTRANSMISSION TO THE INNER EAR

FIELD OF THE INVENTION

The invention relates to devices and methods for the delivery of drugs to the inner ear for treatment of inner ear disorders such as tinnitus. In particular, the invention relates to the use of modulators of L-glutamate-mediated neurotransmission (MGMN). Specifically, the invention relates to delivery of an N-Methyl-D-Aspartate (NMDA) receptor antagonist to the round window niche of the inner ear so as to suppress excessive NMDA receptor-mediated signals, but without causing hearing loss associated with suppression of alpha-amino-3-hydroxy-5-methyl-4-isoxazolepropionate (AMPA) receptor-mediated signals. In particular, the invention encompasses delivering an NMDA receptor antagonist, such as (but not limited to) D-2-amino-5-phosphonopentanoate (D-AP5), Dizocilpine (MK 801), 7-chlorokynurenate (7-CK) and Gacyclidine (GK-11) to the round window niche of the inner ear to treat tinnitus.

BACKGROUND OF THE INVENTION

Any number of insults, such as infections, vascular disorders, or sounds of sufficient intensity and duration will damage the ear and result in temporary or permanent hearing loss. The hearing loss may range from mild to profound, and may also be associated with conditions such as tinnitus, which is the perception of a ringing, roaring, buzzing, or clicking sound etc that occurs inside the head when no external sound is present. Repeated sound overstimulation or other insults cumulative over a lifetime and can cause permanent damage that is not currently treatable. Hearing impairment has a major impact on one's communication ability and even mild impairment may adversely affect the quality of life for millions. Unfortunately, although such hearing loss is preventable, our increasingly noisy environment places more and more people at risk.

L-glutamate (glutamate) is the most important afferent neurotransmitter in the auditory system, and is used by the sensory inner hair cells (IHC) of the cochlea to transduce the mechanical displacement of the basilar membrane into activity of the primary auditory afferent nerve fibers (for a review, see, e.g., Puel (1995) *Neurobiol* 47:449-476). The ionotropic receptors with which glutamate interacts during fast excitatory synaptic transmission include three types of receptors, which are named for their sensitivity to agonists: N-methyl-D-aspartate (NMDA), α-amino-3-hydroxy-5-methyl-4-isoxazolepropionate (AMPA), and kainate. Glutamate can also act through metabotropic receptors (i.e., receptors having activation coupled to an intracellular biochemical cascade). Analysis of glutamate receptors by gene expression, immunocytochemistry, and in situ hybridization indicates that primary auditory nerve cells express NMDA (NR1 and NR2A-D), AMPA (GluR2-4), and kainate (GluR5-7) receptor subunits and the high-affinity kainate-binding proteins (KA1 and KA2) (Puel (1995) supra), suggesting that these receptors all coexist on primary auditory nerve cells.

In addition to its fast excitatory properties, glutamate also plays a role in excitotoxicity, a form of neuronal degeneration in the cochlea, which can occur when, for example, glutamate is released in large amounts or when incompletely recycled in the cochlea. Cochlear excitotoxicity plays a role in ischemic- or noise-induced sudden deafness, as well as in tinnitus (Pujol et al. (1999) *Ann N Y Acad Sci.* 884:249-54; Pujol et al. (1992) *NeuroReport* 3:299-302; Puel et al. (1994) *J. Comp. Neurol.* 341:241-256; Puel (1995), supra).

Excitotoxicity can be generally characterized by a two-step mechanism. In the first phase, glutamate causes overactivation of the ionotropic glutamate receptors that are permeable to cations, which leads to excessive ion permeation, osmotic swelling, free radical generation, and neuronal death. The second phase of glutamate excitotoxicity, which may develop after strong and/or repetitive injury, consists of a cascade of metabolic events triggered by the entry of Ca2+, which leads to neuronal death in the spiral ganglion. Neo-synaptogenesis and functional recovery is accompanied by up-regulation of NMDA and metabotropic glutamate receptors.

Prevention of excitotoxicity has been studied using various antagonists of the ionotropic glutamate receptors. Intracochlear perfusion of the glutamate antagonist kynurenate protects against sound-induced synaptic damage in guinea pigs (Puel et al. (1998) *NeuroReport* 9:2109-2114). Antagonism of the AMPA receptor, e.g., via intracochlear infusion of a selective AMPA receptor antagonist, can block the excitotoxic effect of gultamate in the cochlea. Intracochlear perfusion of 6-7-dinitorquinoxaline-2,3-dione (DNQX) ten minutes prior to or concomitant with AMPA perfusion prevented most of the occurrence of radial dendrite swelling (Puel et al., (1991), supra). Intracochlear perfusion of both DNQX and D-AP5 (a D-2-amino-5-phosphonopentanoate, an NMDA receptor antagonist), provide nearly complete protection of all radial dendrites to AMPA perfusion (Puel et al. (1994) *J. Comp Neurol* 341:241-256). However, use of intracochlear perfusion methods in the clinic is impractical and, on the whole, unacceptable in humans as it would cause permanent damage to the cochlea. Systemic delivery of compounds that modulate glutamate activity, particularly at dosages sufficient to provide for therapy in the inner ear, cause serious aside-effects, such as memory loss and stupor.

As is evident from the above, there is a great need for devices and methods for effective and practical clinical treatment of inner ear disorders such as hearing loss and related conditions such as tinnitus. The present invention addresses this problem.

SUMMARY OF THE INVENTION

The invention features methods and devices for local delivery to the inner ear via the middle ear and delivery of agents that modify glutamate-mediated neurotransmission to the inner ear for treatment of inner ear disorders, such as tinnitus.

In one embodiment, the invention involves delivery of an agent to the inner ear, that modulates synaptic transmission either directly, through interaction of the agent upon the sensory hair cell to decrease glutamate release or upon the neuron to reduce synaptic transmission, or indirectly by modulating an endogenous factor which in turn decrease synaptic transmission (e.g., by administration of a dopamine agonist).

In another related embodiment, the invention involves delivery of an agent that modifies post-synaptic glutamate-mediated neurotransmission, either directly by interacting with a glutamate receptor to decrease glutamate binding (e.g., by decreasing glutamate binding to one or more ionotropic receptors or acting as an antagonist to a glutamate receptor such as an NMDA receptor) or indirectly by modulating an endogenous factor which in turn decreases glutamate binding to a glutamate receptor (e.g., by modulating the glycine site of PCP site).

An animal model has been created in which administration of salicylate produces tinnitus. In this model, excessive signaling is mediated by NMDA receptors, but not by AMPA receptors. The invention uses specific NMDA receptor antagonists to block the excessive signals thereby treating tinnitus.

In particular, the invention encompasses delivering an NMDA receptor antagonist, such as (but not limited to) D-AP5 (D-2-amino-5-phosphonopentanoate, a specific NMDA-antagonist) (Clin Med J (Engl) 2002 January;115(1): 89-93), Dizocilpine (MK 801) (J Neurotrauma 2000 November;17(11):1079-93), 7-chlorokynurenate or Gacyclidine (GK-11) (Curr Opin Investig Drugs 2001 June, 2(6):814-9) onto or in the vicinity of the round window niche of the inner ear to treat tinnitus. The method suppresses excessive NMDA receptor-mediated signals that cause tinnitus, without causing undesired hearing loss associated with suppression of AMPA receptor-mediated signals.

One advantage of the invention is that delivery of drug directly to the inner ear avoids the potential toxicity and side-effects that can be associated with systemic delivery of modulators of glutamate-mediated neurotransmission drug, such as loss of memory or stupor.

In one aspect, the invention features treatment of inner ear disorders by delivering an agent that modulates glutamate-mediated neurotransmission in the inner ear, by perfusion of the agent across the round window membrane.

Another advantage of the invention is that, where the modulator of glutamate-mediated neurotransmission is an NMDA-specific receptor, these drugs have less toxicity in the form of hearing loss than other non-NMDA specific receptor modulators glutamate activity.

Another advantage is that the invention can be used to deliver relatively small quantities of modulators of glutamate-mediated neurotransmission accurately and precisely over a selected period of time. Use of a long-term drug delivery device obviates the need for regular dosing by the patient, thus increasing patient compliance with a prescribed therapeutic regimen, and in particular compliance with a prophylactic regimen prescribed prior to the onset of symptoms.

This is especially useful in populations in which compliance with such medications can be more difficult, e.g., children and the elderly.

Another advantage of the invention is that a modulator of glutamate-mediated neurotransmission can be delivered into the inner ear with such accuracy and precision and at such low quantities as to permit long-term use of such compounds to treat inner ear disorders.

A further advantage is that a therapeutically effective dose of modulators of glutamate-mediated neurotransmission can be delivered at relatively low volume rates, e.g., from about 0.01 µl/day to 2 ml/day so as to minimize disturbance or trauma to the delicate structures of the middle and/or inner ear.

These and other objects, advantages and features of the present invention will become apparent to those persons skilled in the art upon reading the details of the methodology and compositions as more fully set forth below.

BRIEF DESCRIPTION OF THE DRAWINGS

FIG. 2 shows two graphs comparing the affect of acute intracochlear perfusion and chronic round window perfusion. These graphs represent the mean amplitude of the CAP as, the function of the intensity of 8 kHz tone burst stimulation. Mean threshold has been calculated from 5 different animals. Note that both acute intracochlear and chronic round window application of riluzole reduce the CAP amplitude in a dose-dependent manner. However, the effect was 10 times less potent when the drug was applied onto the round window.

FIG. 3 shows the protective effect of riluzole on intense noise induced acoustic trauma. CAP audiograms (threshold shifts as the function of tone frequency) were measured 2 days after 30 minutes of continuous sound exposure. Threshold shift was calculated as the difference in the recording before and 2 days after 6 kHz continuous tone exposure. Shown are threshold shift recorded after 120 dB SPL exposure during 30 minutes in presence of artificial perilymph (red curve, control). Note the clear protection of 100 µM riluzole when either applied directly into the cochlea (blue curve, intra) or onto the round window (green curve, RW). "n" is the number of tested animals

FIG. 5A shows results for the number of positive responses in response to sound, as a percentage of the total (Score %) to sound vs. time in days, with salicylate being delivered between days 2 and 5.

FIG. 5B shows the results for the number of responses without sound (false positives), with salicylate being delivered between days 2 and 5. Using this behavioral paradigm, treatment with saline solution (daily injections during 4 days, i.p.) did not change the score or false positive numbers. In contrast, sodium-salicylate treatment (daily injection, 300 mg/kg/day during 4 days, i.p.) provoked a reversible reduction of the score and a drastic increase of the number of false positives.

FIG. 5C shows the results for compound action potential (CAP) audiograms in behavioral trained animals recorded before (day 0), during (day 3 and day 4) and after salicylate treatment (day 6). CAP thresholds were measured using an electrode chronically implanted on round window in response to a tone burst of 1 ms rise/fall time and 9 ms duration presented at a rate of 10 times per second. Salicylate treatment (daily injection, 300 mg/kg/day during 4 days, i.p.) induced a 30 dB hearing loss across frequency range from 2 to 26 KHz.

FIG. 5D shows CAP threshold shift at 10 kHz before, during and after salicylate treatment. CAP threshold shifts were calculated as the difference in dB between the auditory threshold at day 0 and the auditory threshold at each day. To avoid changes due to hearing loss, the intensity of sound eliciting behavioral responses was adjusted as a function of CAP threshold shift.

FIG. 5E shows that no significant decrease in the score was observed, with salicylate being delivered between days 2 and 5.

FIG. 5F shows that false positive responses still remained after salicylate treatment. This demonstrates that the increased number of false positive responses during sodium-salicylate treatment was due to the occurrence of tinnitus, and not to hearing loss. Gelfoam placed on the round window was used to apply drugs into the fluid of the cochlea. (G) Note that the score remained unchanged. In contrast, round window application of 50 µM of 7-CK blocked the occurrence of false positive responses. Findings indicate that tinnitus induced by sodium-salicylate requires activation of cochlear NMDA receptors. From this experiment it can be concluded that round window perfusion of NMDA antagonists suppresses tinnitus induced by salicylate.

FIG. 6 shows the comparative effects on NMDA antagonists on salicylate-induced tinnitus. Shown are the number of false positive responses measured at the end salicylate treatment (day 4) in animals with gelfoams bathed with artificial perilymph alone (AP, n=10) alone or MK-801 (10 µM, n=10), 7-chlorokynurenate (7-CK, 50 µM, n=10), or gacyclidine (50 µM, n=10). When compared with AP alone, local application of MK-801, 7-CK, or gacyclidine drastically reduced the occurrence of the false positive responses.

DESCRIPTION OF THE PREFERRED EMBODIMENTS

Figure 1:
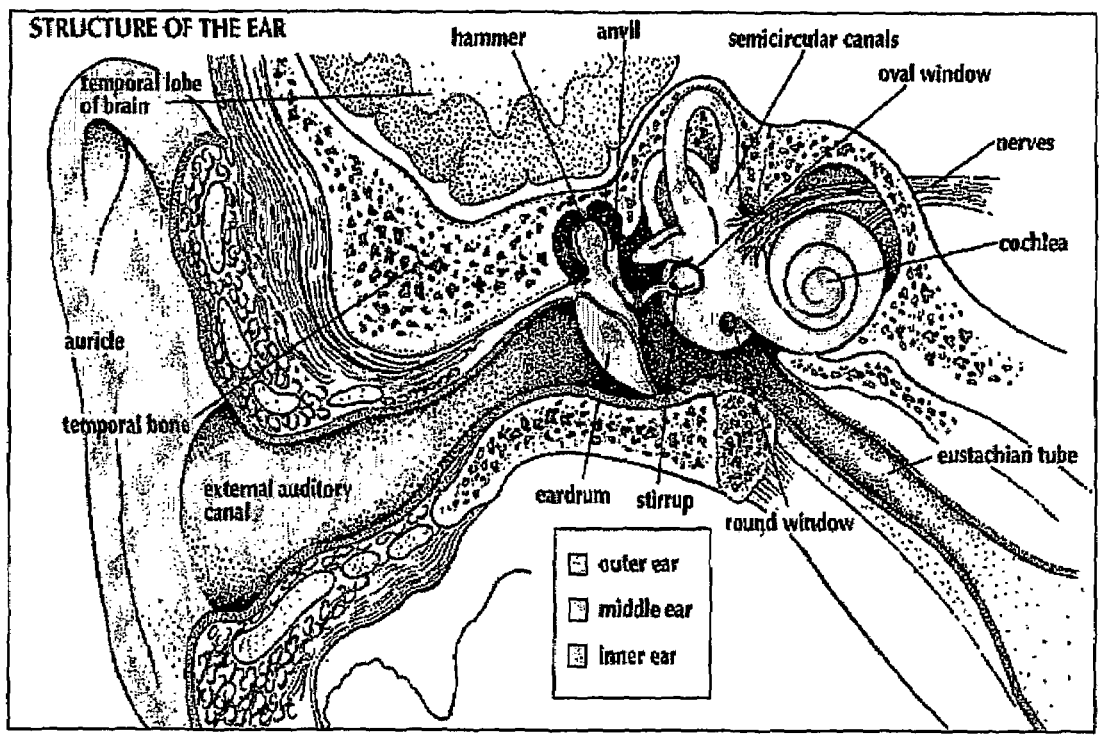
FIG. 1 is a schematic drawing of the ear showing the outer, middle and inner ear, and clearly showing the round window.

Before the present device and methods for treatment of an inner ear disorder are described, it is to be understood that this invention is not limited to the specific methodology, devices, therapeutic formulations, and syndromes described as such may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "and", and "the" include plural referents unless the context clearly dictates otherwise. Thus, for example, reference to "a drug delivery device" includes a plurality of such devices and reference to "the method of delivery" includes reference to equivalent steps and methods known to those skilled in the art, and so forth.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing the compositions and methodologies which are described in the publications which might be used in connection with the presently described invention. The publications discussed herein are provided solely for their disclosure prior to the filing date of the present application. Nothing herein is to be construed as an admission that the invention is not entitled to antedate such a disclosure by virtue of prior invention.

Definitions

The term "inner ear disorder caused by aberrant glutamate-mediated neurotransmission" as used herein refers to conditions that result from overstimulation or understimulation of glutamate receptors, e.g., tinnitus, ischemic-induced sudden deafness, noise-induced sudden deafness, and the like.

The term "subject" is meant any subject, generally a mammal (e.g., human, canine, feline, equine, bovine, ungulate, porcine etc.), in which treatment of an inner ear disorder is desired.

The acronym CAP means Compound Action Potential in microvolts.

The term "implantation site" is used to refer to a site within the body of a subject at which a drug delivery device is introduced and positioned.

The terms "agent that modulates glutamate-mediated neurotransmission," "modulator of glutamate-mediated neurotransmission," "glutamate neuromodulatory agent" are meant to encompass agents that act either directly or indirectly to increases or decreases glutamate release (pre-synaptic modulators of glutamate-mediated neurotransmission) or activity of glutamate in binding to glutamate receptors (post-synaptic modulators of glutamate-mediated neurotransmission).

To call one compound a "derivative" of another compound means that the derivative has been made from or could have been made from the original compound, and shares core structural components.

An "analogue" is a compound related to another compound structurally and functionally; the compound and the analogue share close structural similarity and have a similar biological function, and includes isomers.

A "pharmaceutical composition" is a mixture containing a drug (defined below).

The term "formulation" (or "drug formulation") means any drug together with a pharmaceutically acceptable excipient or carrier such as a solvent such as water, phosphate buffered saline or other acceptable substance. A formulation may comprise one or more agents (drugs) that modulate glutamate-mediated neurotransmission e.g.: NMDA receptor antagonists, AMPA receptor antagonists, and kainate receptor antagonists or components with effects on more than one of said receptor types.

The term "therapeutically effective amount" means an amount of a therapeutic agent, or a rate of delivery of a therapeutic agent, effective to facilitate a desired therapeutic effect. In general, the invention involves alleviating symptoms caused by aberrant glutamate-mediated neurotransmission in the inner ear in a subject suffering from such symptoms or at risk of a condition associated with such symptoms (e.g., a subject who is to be exposed to noise trauma that may be of a level sufficient to induce temporary or permanent hearing loss in the subject due to unacceptably high activity in glutamate-mediated neurotransmission).

The term "sustained release" means release (of a drug) over an extended period of time, as contrasted with "bolus" release. Sustained release, for example, may be for a period of at least 12 hours, at least 24 hours, at least two weeks, at least a month, at least three months, or longer.

The term "drug delivery device" refers to any means for containing and releasing a drug wherein the drug is released into a subject. A drug delivery device may include a catheter via which a drug is delivered. The means for containment is not limited to containment in a walled vessel, but may be any type of containment device, including non-injectable devices (pumps etc) and injectable devices, including a gel, a viscous or semi-solid material or even a liquid. Drug delivery devices are split into five major groups: inhaled, oral, transdermal, parenteral and suppository. Inhaled devices include gaseous, misting, emulsifying and nebulizing bronchial (including nasal) inhalers; oral includes mostly pills; whereas transdermal includes mostly patches. Parenteral includes two subgroups: injectable and non-injectable devices. Non-injectable devices are generally referred to as "implants" or "non-injectable implants" and include e.g., solid biodegradable polymers and pumps (e.g., osmotic pumps, biodegradable implants, electrodiffusion systems, electroosmosis systems, vapor pressure pumps, electrolytic pumps, effervescent pumps, piezoelectric pumps). Injectable devices are split into bolus injections, that are injected and dissipate, releasing a drug all at once, and depots, that remain discrete at the site of injection, releasing drug over time. Depots include e.g., oils, gels, liquid polymers and non-polymers, and microspheres. A drug delivery device of the invention may be attached to a catheter to deliver a drug from the device to the target site. It may also employ a catheter as a drug delivery device, i.e., a closed catheter, essentially a tube with at least one opening at the drug delivery end (but most probably also having an opening at the other end, to allow pressure equilibration as drug is discharged) may be filled with a drug, and inserted into the ear, for example through the tympanic membrane, with the drug delivery end resting in the round window niche, such that the drug will flow out of the catheter into the round window niche. This flow may be accomplished by capillary action as drug is absorbed through the round window and more drug is drawn from the catheter body through the drug delivery end. Many drug delivery devices are described in *Encyclopedia of Controlled Drug Delivery* (1999), Edith Mathiowitz (Ed.), John Wiley & Sons, Inc.

The term "drug" as used herein, refers to any substance meant to alter animal physiology.

The term "dosage form" refers to a drug plus a drug delivery device.

"Patterned" or "temporal" delivery of drug means delivery of drug in a way that changes predictably, e.g., at an increasing, decreasing, substantially constant, or pulsatile, rate or range of rates (e.g., amount of drug per unit time, or volume of drug formulation for a unit time).

The phrase "substantially continuous" means generally uninterrupted for a pre-selected period of drug delivery (in contrast to a period associated with, for example, a bolus injection).

The terms "treat," "treatment," and the like as used herein generally refer to obtaining a desired pharmacologic and/or physiologic effect. The effect may be prophylactic in terms of completely or partially preventing a condition or symptom thereof and/or may be therapeutic in terms of a partial or complete cure for or suppression of a disease and/or adverse effects attributable to the disease. "Treatment" as used herein covers any treatment of an inner ear disorder (including but not limited to hearing loss, tinnitus, and the like) in an animal, particularly a human, and includes: (a) preventing an inner ear disorder from occurring in a subject that may be predisposed but is not at the time displaying symptoms; (b) inhibiting an inner ear disorder, e.g., arresting development of hearing loss or tinnitus or other such disease or disorder; or (c) relieving disease, i.e., causing regression and/or amelioration of the disease.

Overview

The invention is based on the discovery that modulators of glutamate-mediated neurotransmission can be delivered to the inner ear by diffusion through a middle-inner ear membrane (e.g., the round window membrane or the annular ligament of the stapes footplate), and further that such delivery is effective in dampening glutamate-mediated neurotransmission. In particular, the inventors have discovered that an NMDA receptor antagonist, such as, but not limited to, D-AP5, MK 801, 7-chlorokynurenate or gacyclidine may be delivered to the round window niche of the inner ear in such a way as to suppress excessive NMDA receptor-mediated signals, that in certain cases cause tinnitus, but without causing undesired hearing loss associated with suppression of AMPA receptor-mediated signals.

Without being held to theory, delivery of modulators of glutamate-mediated neurotransmission across the round window membrane is effective to dampen the action potential and calcium influx associated with glutamate-mediated neurotransmission. As a result of the dampening of glutamate-mediated neurotransmission, overstimulation of the glutamate receptors is avoided or diminished, and symptoms normally associated with increased glutamate activity are decreased, e.g., hearing can be preserved, tinnitus symptoms are decreased, and the like. If the drug used to dampen neurotransmission is a drug that specifically inhibits NMDA receptor-mediated signals, then one can avoid unwanted effects, such as hearing loss, that are associated with inhibition of AMPA receptor-mediated signals or signals mediated by other receptors.

In view of the above, then, modulation of glutamate-mediated neurotransmission according to the invention can be accomplished in a variety of ways. For example, glutamate-mediated neurotransmission can be modulated pre-synaptically to decrease glutamate release, thereby decreasing stimulation of the glutamate receptors. Pre-synaptic glutamate neuromodulation can be accomplished directly, by administration of an agent that acts to decrease glutamate release.

Post-synaptic glutamate neuromodulation can be accomplished directly by administration of an agent that interacts with one or more glutamate receptors (e.g., to compete with glutamate for binding to the receptor, to bind to the receptor in a manner that affects receptor affinity or avidity for glutamate, or to otherwise decrease the glutamate receptors available for glutamate binding and stimulation). Post-synaptic glutamate neuromodulation can be accomplished indirectly by administration of an agent that increase the levels of an endogenous factor that in turn affects glutamate binding to a glutamate receptor (e.g., by administration of a dopamine agonist).

Alternatively, glutamate-mediated neurotransmission can be modulated by increasing stimulation of glutamate receptors by, for example, directly or indirectly causing an increase release of glutamate (pre-synaptic modulation) or directly or indirectly causing an increase in stimulation of glutamate receptors.

It should be noted that the desired effect of the modulator of glutamate-mediated neurotransmission need not be complete to be effective. For example, where a decrease in glutamate receptor stimulation is desired, the modulator of glutamate-mediated neurotransmission need not entirely block glutamate activity, but rather only provide for a general decrease in glutamate activity in stimulating neurotransmission. Completely blocking glutamate-mediated neurotransmission can result in at least temporary hearing loss (i.e., if there is no glutamate-mediated neurotransmission, then the auditory nerve is not stimulated and the sensation of hearing is lost). Except in instances in which temporary hearing loss as a result of blocking of glutamate-mediated neurotransmission may provide a protective effect against exposure to a stimulus that would result in permanent hearing loss, completely blocking glutamate-mediated neurotransmission is generally undesirable.

Glutamate Neuromodulatory Agents and Formulations

A formulation of the invention will comprise an agent that acts as a direct or indirect modulator of glutamate-mediated neurotransmission through activity pre- or post-glutamate release. Such agents can include, but are not necessarily limited to, agents that directly or indirectly decrease binding of glutamate to an ionotropic glutamate receptor (such as an NMDA receptor, an AMPA, receptor, or a kainite receptor) or a metabotropic receptor (such as mGluR1, 3-5, 7, 8). Further agents include agents that directly or indirectly decrease pre-synaptic release of glutamate. For a review of glutamate antagonists, steroids, and antioxidants suitable for use in the invention in the treatment of inner ear, see Simpson and Davies, (*Trends Pharmacol Sci* 20, 12 (1999).

Exemplary agents include, but are not necessarily limited to, NMDA-specific glutamate antagonists such as D-2-amino-5-phosphonopentanoate (D-AP5), Dizocilpine (MK 801), 7-chlorokynurenate (7-CK) and Gacyclidine (GK-11). Among the NMDA-antagonists, Gacyclidine is considered one of the preferred compounds. Agents that could be used for the invention may also include drugs that mimic or block the action of the lateral efferents, including those that affect neurotransmitters or neuromodulators such as acetylcholine, GABA, dopamine, enkephalins, dynorphins and calcitonin gene-related peptide. Additionally, all drags that act on sodium channel activity such as riluzole, dextromethorophan may be used to treat inner ear disorders such as tinnitus in accordance with the present invention.

Exemplary structures and derivatives or analogues of compounds that may be used for the invention are set out below. Derivatives or analogues useful in the invention may contain additional or alternative substituent (—R) groups at various locations, wherein such substituent groups may be selected from any appropriate group. Substituent groups can be selected by those of skill in the art taking into account charge and size and location of the group to minimize steric hindrance effects and maintain functionality. For example, substituent groups may be individually selected from the group consisting of hydrogen or a halogen and unsubstituted or substituted alkyl, alkenyl and alkynyl of up to 6 carbon atoms.

D-2-amino-5-phosphonopentanoate (D-AP5), has the following chemical structure:

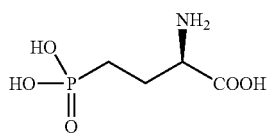

Derivatives or analogues of D-AP5 useful in the invention may contain additional or alternative substituent (—R) groups at various locations as shown.

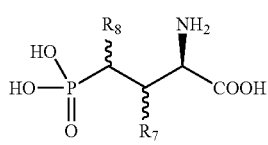

7-chlorokynurenate (7-CK) has the following chemical structure:

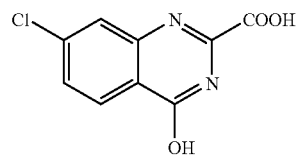

Derivatives or analogues of 7-CK useful in the invention may contain additional or alternative substituent (—R) groups at various locations as shown.

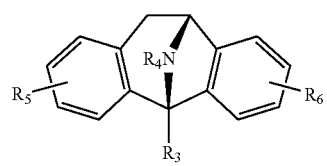

Dizocilpine (MK 801), has the following chemical structure:

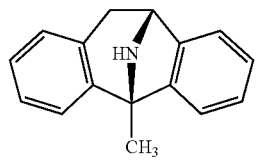

Derivatives or analogues of MK 801 useful in the invention may contain additional or alternative substituent (—R) groups at various locations as shown.

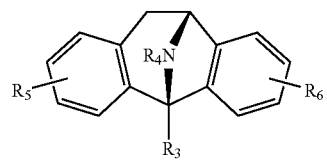

Gacyclidine (GK-11) has the following chemical structure (two racemic structures shown):

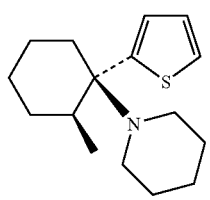 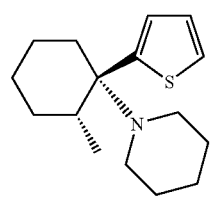

(+) Gacyclidine (GK11)   (−) Gacyclidine (GK11)

Derivatives or analogues of Gacyclidine useful in the invention may contain additional or alternative substituent (—R) groups at various locations as shown.

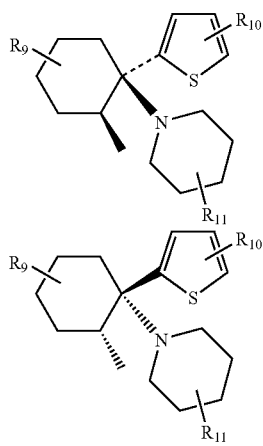

While the agents above are contemplated for delivery according to the invention, variations within the scope of the invention will be readily apparent to the ordinarily skilled artisan upon reading the disclosure provided herein.

The modulator of glutamate-mediated neurotransmission delivered can vary according to a variety of factors, including but not limited to, concurrent therapy (e.g., potential for drug interactions), age of the subject, severity of the disorder, recurrence of symptoms in subject, and the like.

Agents that modulate glutamate-mediated neurotransmission can be provided in any of a variety of formulations compatible with delivery across a middle-inner ear membrane, provided that such formulation is stable (i.e., not subject to degradation to an unacceptable amount at body temperature). The concentration of agent in the formulation may vary from about 0.1 wt. % to about 50 or 75 wt. %. The agent can be provided in any form suitable for delivery and diffusion of agent across the middle-inner ear membrane structure, e.g., solid, semi-solid, gel, liquid, suspension, emulsion, osmotic dosage formulation, diffusion dosage formulation, erodible formulation, etc. In one embodiment, the formulation is suitable for delivery using an implantable pump in connection with a catheter inserted near the round window niche of the inner ear, e.g., an osmotic pump.

Pharmaceutical grade organic or inorganic carriers, excipients and/or diluents can be included in the formulations. The formulations can optionally comprise a buffer such as sodium phosphate at physiological pH value, physiological saline or both (i.e., phosphate buffered saline). Suitable excipients can comprise dextrose, glycerol, alcohol (e.g., ethanol), and the like, and combinations of one or more thereof with vegetable oils, propylene glycol, polyethylene glycol, benzyl alcohol, benzyl benzoate, dimethyl sulfoxide (DMSO), organics, and the like to provide a suitable composition. In addition, if desired, the composition can comprise hydrophobic or aqueous surfactants, dispersing agents, wetting or emulsifying agents, isotonic agents, pH buffering agents, dissolution promoting agents, stabilizers, antiseptic agents and other typical auxiliary additives employed in the formulation of pharmaceutical preparations. Exemplary additional active ingredients that can be present in the formulations useful with the invention can include, but are not limited to, D-AP5, MK 801, 7-chlorokynurenate or gacyclidine.

The modulator of glutamate-mediated neurotransmission can be provided in the formulation as a solution, a suspension, and/or as a precipitate.

Conditions Amenable to Treatment According to the Invention

In general, administration of a formulation according to the invention can be used to treat (e.g., prophylactically or after onset) an inner ear disorder caused by overstimulation of glutamate receptors, e.g., due to aberrantly increased release of glutamate and/or due to defects in glutamate receptor signaling that lead to aberrantly increased glutamate receptor activity. Of particular interest is the management of inner ear disorders that may require long-term therapy, e.g., chronic and/or persistent inner ear disorders (e.g., tinnitus) for which therapy involves treatment over a period of several days (e.g., about 3 days to 10 days), to several weeks (e.g., about 2 weeks or 4 weeks to 6 weeks), to several months or years, up to including the remaining lifetime of the subject. Subjects who are not presently suffering from a disease or condition, but who are susceptible to such, may particularly benefit from prophylactic management using the devices and methods of the invention. Inner ear disorders amenable to therapy according to the invention may involve prolonged episodes alternating with relatively symptom-free intervals, or substantially unremitting symptoms that vary in severity.

Specific examples of conditions, diseases, disorders, and physiological responses amenable to management according to the present invention include, but are not necessarily limited to tinnitus, hearing loss due to cochlear ischemia, noise exposure, presbycusis.

Delivery of Glutamate Neuromodulatory Agents According to the Invention

In general, the glutamate-mediated neurotransmission modulator formulation is delivered at a volume rate that is compatible with delivery to the inner ear via the middle ear, and at a dose that is therapeutically effective in management of a disorder caused by aberrant glutamate-mediated neurotransmission, e.g., overstimulation of glutamate receptors.

In general, administration of a modulator of glutamate-mediated neurotransmission according to the invention can be sustained for several hours (e.g., 2 hours, 12 hours, or 24 hours to 48 hours or more), to several days (e.g., 2 to 5 days or more), to several months or years. Typically, delivery can be continued for a period ranging from several days (1, 2, 7, 14 days) to about 1 month to about three months, or 6 month or 9 months or about 12 months or more. The modulator of glutamate-mediated neurotransmission may be administered to an individual for a period of, for example, from about 2 hours to about 72 hours, from about 4 hours to about 36 hours, from about 12 hours to about 24 hours, from about 2 days to about 30 days, from about 5 days to about 20 days, from about 7 days or more, from about 10 days or more, from about 100 days or more, from about 1 week to about 4 weeks, from about 1 month to about 24 months, from about 2 months to about 12 months, from about 3 months to about 9 months, from about 1 month or more, from about 2 months or more, or from about 6 months or more; or other ranges of time, including incremental ranges, within these ranges, as needed. In particular embodiments, a formulation is delivered to the subject for a preselected period without the need for re-accessing the device and/or without the need for re-filling the device. In these embodiments, formulations having a high-concentration of a modulator of glutamate-mediated neurotransmission are of particular interest.

Preferably, delivery of a formulation of the invention is in a patterned fashion, a substantially continuous fashion, or at a substantially constant, pre-selected rate or range of rates (e.g., amount of agent per unit time, or volume of formulation for a unit time). The agent is preferably delivered at a low volume rate of from about 0.01 µl/day to about 2 ml/day, preferably about 0.04 µl/day to about 1 ml/day, generally about 0.2 µl/day to about 0.5 ml/day, typically from about 2.0 µl/day to about 0.25 ml/day.

Long-term dosages are convenient for the subject, and administration of the long-term dose is simple and can be conducted on an out-patient basis where the patient's health allows such (methods for accomplishing delivery are discussed in more detail below). Long-term delivery also increases patient compliance, and may provide for more accurate dosing (e.g., where a controlled release drug delivery device is used). Implanted drug delivery devices, e.g., osmotic pumps, have an added benefit in that they reduce the risk of infection associated with external pumps or other methods that require repeated breaking of the skin and/or maintenance of a port for administration.

In one embodiment, a drug delivery device provides for substantially continuous, delivery of agent at a preselected rate to a middle-inner ear membrane (e.g., to the round window membrane or annular ligament of the stapes footplate). In this embodiment, the agent can be delivered at a rate of from about 0.1 µg/hr to about 200 µg/hr, usually from about 0.25 µg/hr or 3 µg/hr to about 85 µg/hr, and typically between about 5 µg/hr to about 100 µg/hr. In a specific exemplary embodiment, a modulator of glutamate-mediated neurotransmission is delivered at a rate of from about 0.1 µg/hr, 0.25 µg/hr, 1 µg/hr, generally up to about 200 µg/hr.

Appropriate amounts of a particular modulator of glutamate-mediated neurotransmission can be readily determined by the ordinarily skilled artisan based upon, for example, the relative potency of these drugs, and effectiveness in animal models. The actual dose of drug delivered will vary with a variety of factors such as the potency and other properties of the selected drug used (e.g., hydrophilicity, rate of diffusion across the round window membrane, etc.).

Delivery of glutamate neuromodulatory agents to the inner ear according to the invention can be accomplished in a variety of ways. These include filling the middle ear with a solution or other carrier of the agent (see, e.g., Shea (1997) *Otolaryngol Clin North Am.* 30(6):1051-9. One may also accomplish delivery of agents by insertion of gelatin or Gelfoam™ comprising the agent, see, e.g., Silverstein (1984) *Ann Otol Rhinol Laryngol Suppl.* 112:44-8; Lundman et al. (1992) *Otolaryngol* 112:524; Nedzelski et al. (1993) *Am. J. Otol.* 14:278-82; Silverstein et al. (1996) *Ear Nose Throat J* 75:468-88; Ramsay et al. (1996) *Otolaryngol.* 116:39; Ruan et al. (1997) *Hear Res* 114:169; Wanamaker et al. (1998) *Am. J. Otology* 19:170; Arriaga et al. (1998) *Laryngoscope* 108: 1682-5; and Husmann et al. (1998) *Hear Res* 125:109). One may also accomplish delivery of agents by insertion of hyaluronan or hyaluronic acid mixed with the agent, see, e.g., WO 97/38698; Silverstein et al. (1998) *Am J Otol.* 19(2):196-201; for use of fibrin glue or other fibrin-based vehicles in delivery of agents to the inner ear, see, e.g. Balough et al. (1998) *Otolaryngol. Head Neck Surg.* 119:427-31; Park et al. (1997) *Laryngoscope* 107:1378-81.

Delivery of glutamate neuromodulatory agents to the inner ear according to the invention can be accomplished using the IntraEAR® Round Window µ-Cath™ and Round Window E-Cath™ products, both of which have received marketing clearance from the FDA and European CE Mark approval. The Round Window µ-Cath™ and Round Window E-Cath™ products are dual- and triple-lumen micro-catheters of proprietary design which allow controlled fluid delivery to the round window membrane of the middle ear which physicians have used to treat a variety of ear disorders. These catheters feature a proprietary tip which is designed to allow the surgeon to secure it in the round window niche of the middle ear. These catheters can be left in place for many weeks and can be connected to a syringe or pump (such as those manufactured by Disetronic Medical Systems) for continuous delivery of therapeutic fluids to the inner ear. The dual-lumen design allows the treating physician to add and remove fluid or flush the device without a build-up of air or fluid pressure. The E-Cath design incorporates an additional electrode to allow physicians to record electrical signals related to activities in the ear. Such InnerEar catheters are described in U.S. Pat. Nos. 6,045,528; 5,421,818; 5,476446; and 5,474,529, all expressly incorporated herein by reference. Such catheters can be used in connection with a drug delivery device described below.

Delivery of Drug Using a Controlled Release Device

In general, the drug release methods or devices suitable for use in the invention comprise a drug reservoir for retaining a drug formulation or alternatively some substrate or matrix which can hold drug (e.g., polymer, binding solid, etc.). The drug release device can be selected from any of a variety of implantable drug delivery systems known in the art and suitable for delivery of a drug to the round window, to facilitate perfusion of drug across the round window or other middle-inner ear membrane and into the inner ear.

In specific embodiments, the delivery device is one that is adapted for delivery of a formulation over extended periods of time. Such delivery devices may be adapted for administration of a formulation for several hours to several weeks or longer. Drug delivery provides treatment or prophylaxis against hearing loss, tinnitus, or other inner ear disorders. Generally, the modulator of glutamate-mediated neurotransmission is administered to an individual for at least a week, or at least several weeks, a month, two months, three months, six months a year or longer.

The drug release device of the invention can be based upon a diffusive system, a convective system, or an erodible system (e.g., an erosion-based system). For example, the drug release device can be an osmotic pump, an electroosmotic pump, a vapor pressure pump, or osmotic bursting matrix, e.g., where the drug is incorporated into a polymer and the polymer provides for release of drug formulation concomitant with degradation of a drug-impregnated polymeric material (e.g., a biodegradable, drug-impregnated polymeric material). In other embodiments, the drug release device is based upon an electrodiffusion system, an electrolytic pump, an effervescent pump, a piezoelectric pump, a hydrolytic system, etc.

Where a drug delivery catheter or other delivery device is used in connection with a controlled release device, drug can be delivered through the drug delivery catheter from the reservoir of the controlled release device to the round window membrane as a result of capillary action, as a result of pressure generated from the drug release device, by diffusion, by electrodiffusion or by electroosmosis through the device and/or the catheter, e.g., an IntraEAR® catheter discussed above.

The drug delivery device is generally capable of carrying the drug formulation in such quantities and concentration as therapeutically required, and must provide sufficient protection to the formulation from attack by body processes for the duration of implantation and delivery. The exterior is thus preferably made of a material that has properties to diminish the risk of leakage, cracking, breakage, or distortion so as to prevent expelling of its contents in an uncontrolled manner under stresses it would be subjected to during use. The drug reservoir must be biocompatible (e.g., substantially non-reactive with respect to a subject's body or body fluids).

Suitable materials are well known in the art. For example, the reservoir material may comprise a non-reactive polymer or a biocompatible metal or alloy. Suitable polymers include, but are not necessarily limited to, acrylonitrile polymers such as acrylonitrile-butadiene polymer, and the like; halogenated polymers such as polytetrafluoroethylene, polyurethane, polychlorotrifluoroethylene, copolymer tetrafluoroethylene and hexafluoropropylene; polyethylene vinylacetate (EVA), polyimide; polysulfone; polycarbonate; polyethylene; polypropylene; polyvinylchloride-acrylic copolymer; poly-carbonate-acrylonitrile-butadienestyRemy; polystyRemy; cellulosic polymers; and the like. Further exemplary polymers are described in The Handbook of Common Polymers, Scott and Roff, CRC Press, Cleveland Rubber Co., Cleveland, Ohio.

Metallic materials suitable for use in the reservoir of the drug release device include stainless steel, titanium, platinum, tantalum, gold and their alloys; gold-plated ferrous alloys; platinum-plated titanium, stainless steel, tantalum, gold and their alloys as well as other ferrous alloys; cobalt-chromium alloys; and titanium nitride-coated stainless steel, titanium, platinum, tantalum, gold, and their alloys.

Exemplary materials for use in polymeric matrices include, but are not necessarily limited to, biocompatible polymers, including biostable polymers and biodegradable polymers. Exemplary biostable polymers include, but are not necessarily limited to silicone, polyurethane, polyether urethane, polyether urethane urea, polyamide, polyacetal, polyester, poly ethylenechlorotrifluoroethylene, polytetrafluoroethylene (PTFE or "Teflon™"), styRemy butadiene rubber, polyethylene, polypropylene, polyphenylene oxide-polysty-Remy, poly-a-chloro-p-xylene, polymethylpentene, polysulfone and other related biostable polymers. Exemplary biodegradable polymers include, but are not necessarily limited to, polyanhydrides, cyclodestrans, polylactic-glycolic acid, polyorthoesters, n-vinyl alcohol, polyethylene oxide/polyethylene terephthalate, polyglycolic acid, polylactic acid and other related bioabsorbable polymers.

Another well-known drug delivery device is a "depot" which is an injectable biodegradable sustained release device that is generally non-containerized and that may act as a reservoir for a drug, and from which a drug is released. Depots include polymeric and non-polymeric materials, and may be solid, liquid or semi-solid in form. For example, a depot as used in the present invention may be a high viscosity liquid, such as a non-polymeric non-water-soluble liquid carrier material, e.g., Sucrose Acetate Isobutyrate (SAIB) or another compound described in U.S. Pat. Nos. 5,747,058 and 5,968,542, both expressly incorporated by reference herein. For reference, please refer generally to "Encyclopedia of Controlled Drug Delivery" 1999, published by John Wiley & Sons Inc, edited by Edith Mathiowitz. SAIB may be formulated, for example, with one or more solvents, including but not limited to, nonhydroxylic solvents such as benzyl benzoate, N-methyl-2-pyrrolidone (NMP), dimethylsulfoxide (DMSO), or mixtures thereof. In certain embodiments, it may be desirable to use a solvent such as ethanol, methanol, or glycerol. Where the formulation is to be administered as a spray, a propellant may be added. The solvent can be added to SAIB in a ratio of from about 5% to about 50% solvent.

An exemplary device for controlled delivery of drug to the inner ear according to the invention is described in PCT Publication No. WO 00/33775. This device generally comprises a drug delivery unit comprising a carrier media material comprising one or more therapeutic agents. The carrier media material is designed to release the agent in a controlled manner over time, and is shaped and sized for placement of at least portion of the device in the round window niche.

Drug release devices based upon a mechanical or electromechanical infusion pump, can also be suitable for use with the present invention, generally with an operably connected catheter which is implanted for delivery of drug to the round window membrane. Examples of such devices include those described in, for example, U.S. Pat. Nos. 4,692,147; 4,360,019; 4,487,603; 4,360,019; 4,725,852, and the like. In general, the present methods of drug delivery can be accomplished using any of a variety of refillable, non-exchangeable pump systems. Pumps and other convective systems are generally preferred due to their generally more consistent, controlled release over time. Osmotic pumps are particularly preferred due to their combined advantages of more consistent controlled release and relatively small size. Of the osmotic pumps, the DUROS™ osmotic pump is particularly preferred (see, e.g., WO 97/27840 and U.S. Pat. Nos. 5,985, 305 and 5,728,396)).

In one embodiment, the drug release device is a continuous drug release device in the form of an osmotically-driven device. Preferred osmotically-driven drug release systems are those that can provide for release of drug in a range of rates of from about 0.1 μg/hr to about 200 μg/hr, and which can be delivered at a volume rate of from about 0.25 μl/day to about 100 μl/day (i.e., from about 0.0004 μl/hr to about 4 μl/hr), preferably from about 0.04 μl/day to about 10 μl/day, generally from about 0.2 μl/day to about 5 μl/day, typically from about 0.5 μl/day to about 1 μl/day. In one embodiment, the volume/time delivery rate is substantially constant (e.g., delivery is generally at a rate ± about 5% to 10% of the cited volume over the cited time period, e.g., a volume rate of about In general, the drug delivery devices suitable for use in the invention are those that can deliver drug at a low dose, e.g., from about 0.1 μg/hr to about 200 μg/hr, and preferably at a low volume rate e.g., on the order of nanoliters to microliters per day. In one embodiment, a volume rate of from about 0.01 μl/day to about 2 ml/day is accomplished by delivery of about 80 μl/hour over a period of 24 hours, with the delivery rate over that 24 hours period fluctuating over that period by about ±5% to 10%. Exemplary osmotically-driven devices suitable for use in the invention include, but are not necessarily limited to, those described in U.S. Pat. Nos. 3,760,984; 3,845,770; 3,916,899; 3,923,426; 3,987,790; 3,995,631; 3,916,899; 4,016,880; 4,036,228; 4,111,202; 4,111,203; 4,203,440; 4,203,442; 4,210,139; 4,327,725; 4,627,850; 4,865,845; 5,057,318; 5,059,423; 5,112,614; 5,137,727; 5,234,692; 5,234,693; 5,728,396; and the like.

Delivery Using a Drug Delivery Catheter

In some embodiments it may be desirable to provide a drug delivery catheter with the drug delivery device, e.g., where the implantation site and the desired delivery site are not the same. The drug delivery catheter is generally a substantially hollow elongate member having a first end (or "proximal" end) associated with the drug release device of the drug delivery device, and a second end (or "distal" end) for delivery of the drug-comprising formulation to a desired delivery site. Where a drug delivery catheter is used, a first end of the drug delivery catheter can be operably connected to a drug delivery device so that the lumen of the drug delivery catheter is in communication with the drug reservoir in the drug delivery device, so that a formulation contained in a drug reservoir can move into the drug delivery catheter, and out a delivery outlet of the catheter which is positioned for delivery of agent to the round window membrane. In one embodiment, the catheter is positioned at least partially within the round window niche so as to provide for deliver of agent to the round window membrane.

The body of the catheter defines a lumen, which lumen is to have a diameter compatible with providing leak-proof delivery of drug formulation. Where the drug delivery device dispenses drug by convection (as in, e.g., osmotic drug delivery systems), the size of the catheter lumen leading from the reservoir of the drug release system can be designed as described by Theeuwes (1975) J. Pharm. Sci. 64:1987-91.

The body of the catheter can be of any shape (e.g., curved, substantially straight, tapered, etc.). The distal end of the drug delivery catheter can have one or a plurality of openings.

The drug delivery catheter may be produced from any of a variety of suitable materials. Impermeable materials suitable for use in production of the controlled drug release device as described above are generally suitable for use in the production of the drug delivery catheter. Exemplary materials include, polymers; metals; glasses; polyolefins (high density polyethylene (HDPE), low density polyethylene (LDPE), linear low density polyethylene (LLDPE), polypropylene (PP), and the like); nylons; polyethylene terephtholate; silicones; urethanes; liquid crystal polymers; PEBAX®; HYTREL®; TEFLON®; perflouroethylene (PFE) perflouroalkoxy resins (PFA); poly(methyl methacrylate) (PMMA); multilaminates of polymer, metals, and/or glass; nitinol; and the like.

The drug delivery catheter can comprise additional materials or agents (e.g., coatings on the external or internal catheter body surface(s)) to facilitate placement of the drug delivery catheter and/or to provide other desirable characteristics to the catheter. For example, the drug delivery catheter inner and/or outer walls can be coated with silver or otherwise coated or treated with antimicrobial agents, thus further reducing the risk of infection at the site of implantation and drug delivery.

In one embodiment, the drug delivery catheter is primed with a drug-comprising formulation, e.g., is substantially pre-filled with drug prior to implantation. Priming of the drug delivery catheter reduces delivery start-up time, i.e., time related to movement of the drug from the drug delivery device to the distal end of the drug delivery catheter.

Devices for Use in the Invention

Delivery of a glutamate neuromodulatory agent to a middle-inner ear membrane (e.g., the round window niche for perfusion across the round window membrane or annular ligament of the stapes footplate) can be accomplished through use of a delivery device such as those described in described in U.S. Pat. Nos. 5,421,818, which describe various treatment systems comprising a reservoir for a therapeutic agent and, in various embodiments, a fluid transfer means (e.g. pores, a semi-permeable membrane, and the like) which allows fluid materials to be delivered to, for example, the round window membrane for subsequent diffusion into the inner ear. In another embodiment, the device comprises a plurality of reservoir portions and multiple stem portions designed for implantation into, for example, the endolymphatic sac and duct using standard microsurgical techniques. In still another embodiment, the apparatus comprises a reservoir portion for retaining liquid medicine materials therein, and first and second stems. The second stem can reside within the patient's external auditory canal lateral to the ear drum, with the first stem residing within, for example, an opening formed in the stapes footplate/annular ligament so that medicine materials can be delivered to the inner ear from the reservoir portion.

Another device suitable for use in the invention is described in U.S. Pat. No. 6,045,528. The device described in this patent comprises one or more fluid transfer conduits connected to a cover member that can be placed over or at least partially within the round window niche, and in some embodiments forms a liquid resistant fluid-receiving zone within the round window niche. The cover member can be a plate-like structure or can comprise a compressible material.

PCT Publication No. WO 00/04854 describes another device suitable for use in the invention, which device comprises a fluid transfer conduit comprising one or more passageways therethrough. An inflatable bladder attached to the conduit, and is sized for insertion at least partially within an internal cavity of the ear (e.g., the round window niche). When inflated, the bladder engages the internal side wall of the internal cavity to secure the bladder and part of the conduit within the internal cavity, thus allowing transfer of fluids to and from the internal cavity.

Implantation and Delivers Sites

In a particular embodiment, a drug delivery device can be implanted at any suitable implantation site using methods and devices well known in the art. Implantation sites include, but are not necessarily limited to a subdermal, subcutaneous, intramuscular, or other suitable site within a subject's body, e.g., at a subcutaneous site near the ear, e.g., behind the external auditory meatus of the ear. Subcutaneous implantation sites are preferred because of convenience in implantation and removal of the drug delivery device. Delivery of drug from a drug delivery device at an implantation site that is distant from a delivery site can be accomplished by providing the drug delivery device with a catheter.

The drug delivery device can be entirely or at least partially within an internal cavity of the ear, and, in a preferred embodiment, at least partially within the round window niche, e.g., either spaced apart from the round window membrane or positioned against and/or adjacent the membrane.

Many different methods may be used to insert the agent, or device comprising the agent, into the ear for delivery of agent to a middle-inner ear membrane. For example, agent formulation can be injected into the middle ear through the tympanic membrane, and may be specifically placed within, for example, the round window nice to facilitate contact of the agent formulation with a middle-inner ear membrane. Alternatively a drug delivery device can be inserted into the middle ear for delivery of agent to the middle ear, or more directly to the round window membrane structure. In another embodiment, a drug delivery device is positioned external to the middle ear, and a catheter or other drug delivery conduit operably attached to the drug delivery device provides for delivery of drug from a reservoir of the device and to the middle ear, e.g., to the round window membrane.

Insertion of a drug delivery device can be accomplished by passing the device or a portion of the device (using an appropriate microsurgical instrument of conventional design) through or under the tympanic membrane. The tympanic membrane preferably has an incision that allows the drug delivery device, or a portion thereof, to pass through. Alternatively, the device or a portion thereof can be inserted into the middle ear beneath a tympanomeatal flap. Proper orientation and/or insertion of a drug delivery device can be accomplished through the use of a conventional operating microscope or otologic endoscope apparatus for example of the type disclosed in U.S. Pat. No. 5,419,312 to Arenberg et al.

Placement of the drug delivery device is in a manner so that drug from the device will come in contact with at least a portion of a middle-inner ear membrane. Packing materials of the type normally used for medical applications can be employed within the ear to secure the drug delivery device in its desired position within an internal cavity of the ear. Agent is released from the drug delivery device upon reaching the round window membrane, and travels through a membrane or other structure that provides an interface between the middle and inner ear, and into the inner ear.

In general, the drug delivery systems and methods provide numerous benefits and capabilities including: (1) the repeatable and sustained delivery of therapeutic agents into the inner ear through the round window membrane; (2) the delivery of many different therapeutic agents (e.g. pharmaceutical preparations) to the inner ear in a safe and direct manner; (3) the accomplishment of effective drug delivery without overly invasive surgical procedures; and (4) the use of a simplified method to deliver therapeutic agents into the inner ear of a patient without complex medical procedures, monitoring, and patient discomfort.

EXAMPLES

Methods and Materials

Animal Model of Human Inner Ear.

Experiments were performed on adult guinea pigs weighing from about 250 g to 300 g. The animals were anaesthetized with urethane (1.4 g/kg, i.p.) and artificially respired. Supplemental doses of urethane (0.35 g/kg, i.p.) were administered every 2 hr, or more often if the animal withdrew its paw in response to pressure applied to the paw. The rectal temperature was maintained at about 38.5±1° C., and heart rate (normal range 260-330 beats/min) monitored using EKG electrodes. The external auditory canal was opened near the tympanic annulus, exposing the tympanic membrane and allowing sound to reach the drum without any obstruction. At the end of the experiment, the animals were euthanized by intracardiac injection of an overdose of sodium pentobarbitone.

Intracochlear Perfusion.

Methods for intracochlear perfusion were generally performed as described in Puel 1995 Neurobiology 47:449-476. Briefly, after the cochlea was exposed ventrally and the middle ear muscles severed, 10-min perfusions of a selected drug were performed through a hole made in the scala tympani, at the rate of 2.5 microliters/min, and the drug was allowed to flow out of the cochlea through a hole made in the scala vestibuli. Measurements were taken before and after perfusion of placebo, and after cumulative perfusion of increasing concentrations of agent. At the end of each experiment, the cannula was flushed with artificial perilymph to evaluate the reversibility of the agent's effect. The artificial perilymph solution had the following compositions: 1.37 mM NaCl; 5 mM KCl; 2 mM $CaCl_2$; 1 mM $MgCl_2$; 1 mM $NaHCO_3$; 11 mM glucose, pH 7.4, osmolarity (302±4.2 mosmol/kg $H_2O$). Five to ten guinea pigs were used in each experimental group.

D-AP5 and MK 801 was formulated by dissolution in water to a final concentration varying from 1 to 1000 micromolar, 7-chlorokinurenate and gacyclidine was dissolved in 100% DMSO to final concentrations of from 1 to 100 micromolar.

Perfusion Across the Round Window Membrane.

Drugs were delivered to the round window membrane at the rate of 1 µl drug solution per hour using an animal RWE-Cath™ attached to an Alzet™ Osmotic Pump for up to 14 days, providing a model of chronic delivery to the inner ear. The Alzet™ Osmotic Pump was primed with the highest concentration that did not cause change in the CAP amplitude, increase in CAP latency or decrease in CM amplitude in intracochlear perfusion experiments.

Experiments were performed in order to determine the highest concentration of agent that provides a significant beneficial effect, but does not cause a change in the CAP amplitude, CAP latency, or decrease CM amplitude. If the concentration of drug did change the CAP amplitude, increase the CAP latency, or decrease the CM amplitude, lower concentrations (not lower flow rates) were tested. If the concentration of drug did not change the CAP amplitude, increase the CAP latency, or decrease the CM amplitude, higher concentrations (not higher flow rates) were tested. Five guinea pigs were used in each experimental group.

Stimulation and Recording Technique.

Tone bursts (1 ms rise/fall time, 9 ms duration) were generated by an arbitrary function generator (LeCroy Instrument type 9100R) at a rate of 10 times per second. Acoustic stimuli were amplified and delivered in a closed system via a Bruel and Kjaer microphone (type 4134). Intensity amplitude-functions were obtained by varying tone burst intensities (0-100 dB SPL (Sound Pressure Level) in 5 dB steps). The compound action potential of the auditory nerve (CAP: $N_1$-$P_1$), $N_1$ latency, cochlear microphonic (CM) and summating potential (SP) were recorded from a silver electrode coated with Teflon (except for the tip) placed in a third hole made in the scala vestibuli of the basal turn of te choclea. The potentials were amplified (Tektronic TM 503, gain 1000) averaged (256 samples) and stored on a Pentium PC computer. The sampling rate of the A/D converter was 50 kHz with a dynamic range of 12 bits and 1024 samples per record. The threshold of the CAP was defined as the dB SPL needed to elicit a measurable response ($\geqq 1$ micro Volt).

Statistical analysis. Analysis of variances (ANOVA) and Newmann-Keuls multiple range test were used to determine the significance (p<0,05) of agent effects. Data is expressed as the mean ± standard error.

Salicylate Tinnitus Model. Salicylate, the active component of aspirin, is of special concern in auditory science because it induces tinnitus in humans. The efficacy of agents to treat tinnitus was tested by measuring firing rate of the auditory nerve fibers in presence of salicylate.

The method of recording single unit responses from the auditory nerve during direct application of drugs into the cochlea has been already described elsewhere (J. Ruel, C. Chen, R. Pujol, R. P. Bobbin, J. L. Puel, *J Physiol.* 518, 667, 1999). Briefly, the test solutions were applied into the cochlea using a multi-barrel perfusion pipette (ASI Instruments) placed into a hole made in the basal turn scala tympani and allowed to flow out of the cochlea through a hole (0.2 mm diameter) made at the apex. The cochlear nerve was exposed using a posterior fossa approach. Extracellular action potentials from single auditory nerve fibers were recorded with glass microelectrodes. Once a single unit was isolated, spontaneous activity was averaged over 10 seconds. The unit's tuning curves were then determined by a computer-controlled, threshold-tracking program using a 200 ms tone burst presented at 3/s. The threshold criterion was a difference of 10 spikes/s, i.e., 2 spikes difference between the tone (200 ms) and non-tone (200 ms) counting intervals. The program determined the characteristic frequency (CF) and the frequency tuning of the fiber by measuring the $Q_{10dB}$ defined as the CF divided by the bandwidth at 10 dB above the CF threshold.

A critical step in the initiation of the action potential is the activation of the postsynaptic receptors by the glutamate (Glu), the endogenous neurotransmitter released by the sensory inner hair cells (elsewhere (J. Ruel, C. Chen, R. Pujol, R. P. Bobbin, J. L. Puel, *J Physiol.* 518, 667, 1999). The hypothesis that sodium-salicylate modulates fast cochlear synaptic neurotransmission by acting on alpha-amino-3-hydroxy-5-methyl-4-isoxasole-propionate (AMPA) receptors was proposed. As shown in FIG. 1b, blocking AMPA receptors with 50 µM the AMPA agonist GYKI 53784 (Neuropharm. 30 1959-1973, 2000) blocked both spontaneous activity and those evoked induced by sodium-salicylate or sound. Another possibility was an action of salicylate on N-Methy-D-Aspartate (NMDA) receptors. Although intracochlear perfusion of 10 µM MK-801, 50 µM gacyclidine or 50 µM 7-chlorokynurenic acid (7-CK) had no effect on spontaneous activity of the auditory fibers, NMDA antagonists suppressed neural excitation induced by sodium-salicylate (FIG. 1c). Thus, excitatory action of sodium-salicylate on auditory nerve activity requires the activation of cochlear NMDA.

Example 1

The Comparative Effect of Acute Intracochlear Perfusion and Chronic Round Window Perfusion of Riluzole Because acute intracochlear perfusion (AICP) is not practical in humans, the inventors investigated whether a safe and therapeutic effect could be achieved via round window choclear perfusion (RWCP).

The comparative effect of acute intracochlear perfusion and chronic round window perfusion was investigated. Results are shown in FIG. 2, in which the graphs represent the mean amplitude of the CAP as the function of the intensity of 8 kHz tone burst stimulation. Mean threshold was calculated from 5 different animals. Note that both acute intracochlear and chronic round window application of Riluzole reduce the CAP amplitude in a dose-dependent manner. However, the effect was 10 times less potent when the drug was applied onto the round window. The aim of the study was to compare the effect of acute intracochlear perfusion (AICP) with chronic round window perfusion (CRWP) on the normal functioning of the cochlea. These graphs (FIG. 2) represent the mean amplitude of the CAP as the function of the intensity of 8 kHz tone burst stimulation. Mean threshold has been calculated from 5 different animals. Graph A shows acute intracochlear window application of Riluzole reduced the CAP amplitude. Graph B shows chronic round window application of Riluzole also reduced the CAP amplitude in the dose dependent manner. Note the need to increase concentration by 10 times to get the same effect on CAP. From this experiment it can be concluded that Riluzole retains its activity in the inner ear following chronic perfusion across the round window membrane.

Example 2

The Protective Effect of Riluzole on Intense Noise Induced Acoustic Trauma

As has already been shown, acute cochlear perfusion of Riluzole rescues hearing after noise induced hearing loss (Wang et al., *Neuroscience* 2002, 111,635-648). An experiment was done to determine the protective effect of Riluzole on intense noise induced acoustic trauma. The results are shown in FIG. 3, which shows CAP (Compound Action Potential) audiograms (threshold shifts as the function of tone frequency) were measured 2 days after 30 minutes of continuous sound exposure. Threshold shift was calculated as the difference in the recording before and 2 days after 6 kHz continuous tone exposure. Shown are threshold shift recorded after 120 dB SPL exposure during 30 minutes in presence of artificial perilymph (red curve, control). Note the clear protection of 100 µM Riluzole when either applied directly into the cochlea (blue curve, intra) or onto the round window (green curve, RW). The letter "n" represents the number of tested animals The goal of this experiment was to prove that Riluzole is effective in protecting the inner ear from noise trauma when applied onto the round window membrane. Control animals were implanted with an osmotic mini-pump containing artificial perilymph alone. Exposure to 120 dB SPL pure tone (6 kHz, for 30 min.) immediately (within 20 min) resulted in 50-60 dB permanent threshold shift 2 days after sound exposure (see Wang et al., *Neuroscience*, in press). When 100 µM Riluzole was applied into the cochlea, a clear recovery of threshold was observed. The same effect was obtained when Riluzole was applied onto the round window. From this experiment it can be concluded that perfusion of Riluzole onto the round window membrane is effective in protecting the inner ear from noise trauma.

Example 3

Effect of Perfusion of Glutamate Antagonists on Salicylate—Induced Excitation

An experiment was carried out to determine the ability of perfused Glutamate antagonists to suppress salicylate-induced excitation. The results are shown in FIG. 4.

Figure 4A:
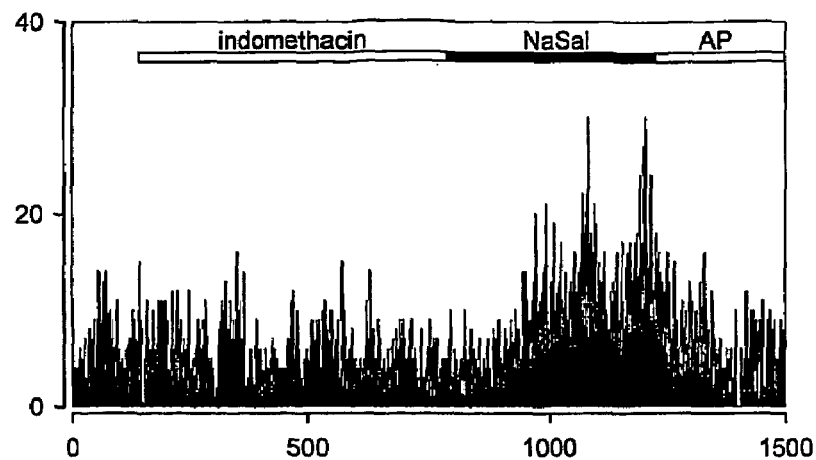
FIG. 4A shows the results of an experiment to determine the ability of perfused Glutamate antagonists to suppress salicylate-induced excitation the results from an original recording from an auditory nerve fiber coding for 8 kHz with a spontaneous rate of 8 spikes $s^{-1}$. Intracochlear perfusion of control artificial periphymph (AP) containing 100 µM indomethacin (open bar) did not change the spontaneous activity of the auditory nerve fiber. In contrast, application of 5 mM of sodium-salicylate (NaSal; black bar) reversibly increased spontaneous firing of the auditory nerve fibers.

FIG. 4A shows the results from an original recording from an auditory nerve fiber coding for 8 kHz with a spontaneous rate of 8 spikes $s^{-1}$. Intracochlear perfusion of control artificial periphymph (AP) containing 100 µM indomethacin (open bar) did not change the spontaneous activity of the auditory nerve fiber. In contrast, application of 5 mM of sodium-salicylate (NaSal; black bar) reversibly increased spontaneous firing of the auditory nerve fibers.

Figure 4B:
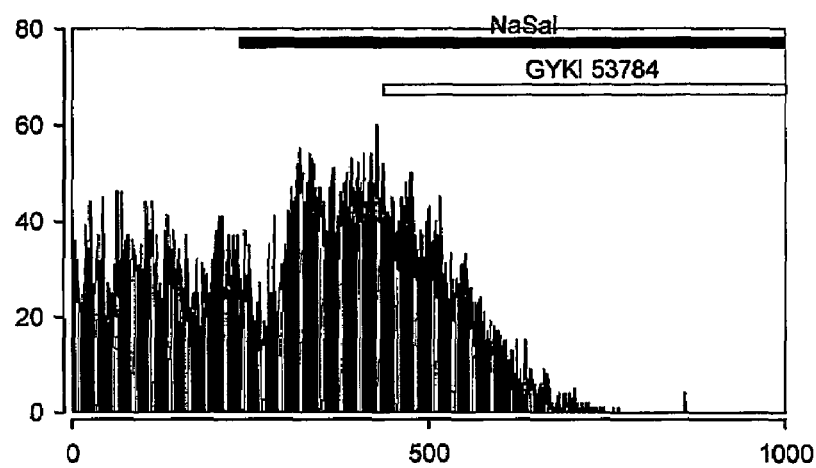
FIG. 4B shows results from a nerve fiber coding for 9 kHz with a spontaneous rate activity of 7 spikes $s^{-1}$. Blocking of AMPA receptors with 50 µM of the AMPA agonist GYKI 53784 (Neuropharm. 30 1959-1973, 2000) (open bar) blocked both the spontaneous and the evoked activity by 5 mM NaSal (black bar).

FIG. 4B shows results from a nerve fiber coding for 9 kHz with a spontaneous rate activity of 7 spikes $s^{-1}$. Blocking of AMPA receptors with 50 µM the AMPA agonist GYKI 53784 (Neuropharm. 30 1959-1973, 2000) (open bar) blocked both the spontaneous and the evoked activity by 5 mM NaSal (black bar).

Figure 4C:
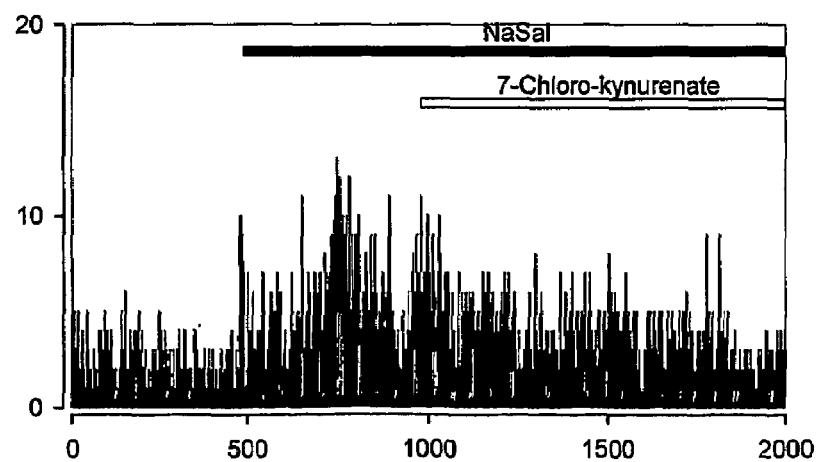
FIG. 4C shows results from a nerve fiber coding for 7.5 kHz with a spontaneous rate of 5 spikes $s^{-1}$. Sodium-salicylate was continuously applied. Repetitive application (Open bars) with the NMDA antagonist 7 CK (50 µM, n=5) suppressed neural excitation of auditory nerve induced by Na Salicylate, but not the spontaneous activity of the fiber.
Figure 4D:
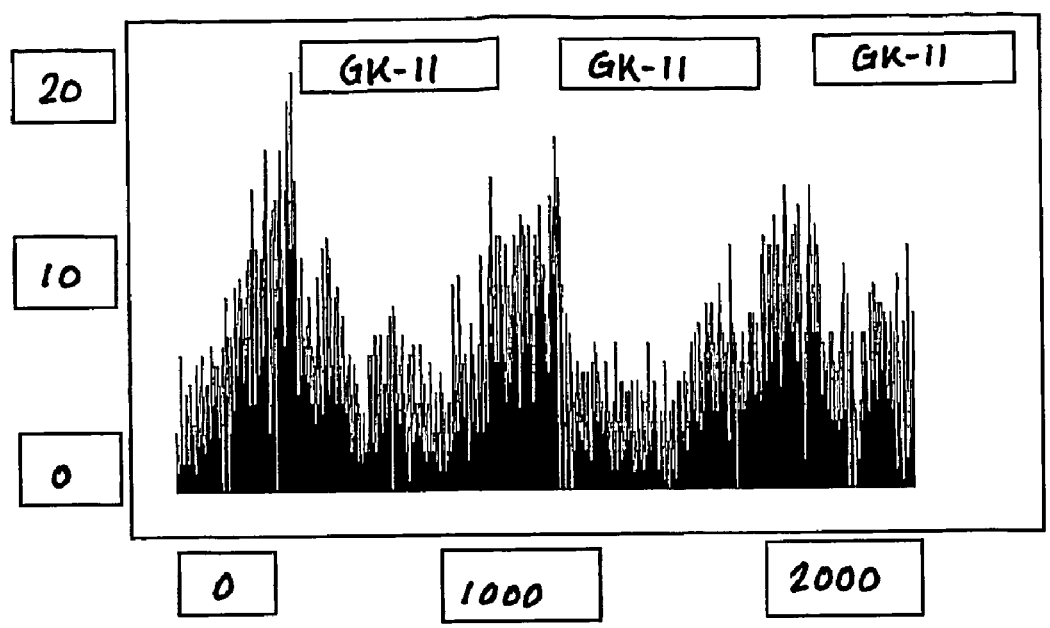
FIG. 4D shows that repetitive application of the NMDA antagonist gacyclidine (50 µM, n=5) suppressed neural excitation of auditory nerve induced by Na Salicylate, but not the spontaneous activity of the fiber.

FIG. 4C shows results from a nerve fiber coding for 7.5 kHz with a spontaneous rate of 5 spikes $s^{-1}$. Sodium-salicylate was continuously applied. Repetitive application (Open bars) with the NMDA antagonist 7 CK (50 µM, n=5) suppressed neural excitation of auditory nerve induced by NaSal, but not the spontaneous activity of the fiber Similar results were obtained with 10 µM MK 801 and GK-11. Thus, excitatory action of sodium-salicylate on auditory nerve activity requires the activation of cochlear NMDA, but not AMPA receptors. From this experiment it can be concluded that perfusion of glutamate antagonists suppressed excitation of the auditory nerve induced by salicylate Example 4

Effect of NMDA Antagonists on Salicylate—Induced Tinnitus

To verify that the excitatory action of sodium-salicylate on the auditory nerve fibers results in perception of tinnitus, a behavioral model was designed in rats based upon an active avoidance task. Animals were trained to respond to a conditioned stimulus consisting of a 10 kHz tone burst of 3 s duration. Experiments were carried out and the results are shown in FIG. 5.

FIG. 5A shows results for the number of positive responses in response to sound, as a percentage of the total (Score %) to sound vs. time in days, with salicylate being delivered between days 2 and 5.

FIG. 5B shows the results for the number of responses without sound (false positives), with salicylate being delivered between days 2 and 5. Using this behavioral paradigm, treatment with saline solution (daily injections during 4 days, i.p.) did not change the score or false positive numbers. In contrast, sodium-salicylate treatment (daily injection, 300 mg/kg/day during 4 days, i.p.) provoked a reversible reduction of the score and a drastic increase of the number of false positives.

FIG. 5C shows the results for compound action potential (CAP) audiograms in behavioral trained animals recorded before (day 0), during (day 3 and day 4) and after salicylate treatment (day 6). CAP thresholds were measured using an electrode chronically implanted on round window in response to a tone burst of 1 ms rise/fall time and 9 ms duration presented at a rate of 10 times per second. Salicylate treatment (daily injection, 300 mg/kg/day during 4 days, i.p.) induced a 30 dB hearing loss across frequency range from 2 to 26 KHz.

FIG. 5D shows CAP threshold shift at 10 kHz before, during and after salicylate treatment. CAP threshold shifts were calculated as the difference in dB between the auditory threshold at day 0 and the auditory threshold at each day. To avoid changes due to hearing loss, the intensity of sound eliciting behavioral responses was adjusted as a function of CAP threshold shift.

FIG. 5E shows that no significant decrease in the score was observed, with salicylate being delivered between days 2 and 5.

FIG. 5F shows that false positive responses still remained after salicylate treatment. This demonstrates that the increased number of false positive responses during sodium-salicylate treatment was due to the occurrence of tinnitus, and not to hearing loss. Gelfoam placed on the round window was used to apply drugs into the fluid of the cochlea. (G) Note that the score remained unchanged. In contrast, round window application of 50 µM of 7-CK blocked the occurrence of false positive responses. Findings indicate that tinnitus induced by sodium-salicylate requires activation of cochlear NMDA receptors. From this experiment it can be concluded that round window perfusion of NMDA antagonists suppresses tinnitus induced by salicylate.

Example 4

Comparative Effect of NMDA Antagonists on Salicylate—Induced Tinnitus

To support the hypothesis that salicylate induced false positive via cochlear NMDA receptors, we applied other NMDA antagonists into the perilymphatic fluids using gelfoam placed on the round window of both ears. Local application of control artificial perilymph did not influence the decrease of the score (FIG. 6) or the increase of the number of false positive responses induced by salicylate (FIG. 6). In contrast, local application of 10 µM of MK 801; 50 µM of 7-CK or 50 µM of gacyclidine strongly reduced the occurrence of false positive responses induced by salicylate, the reduction of the score still been unchanged (FIG. 6). When compared with the control artificial perilymph animals at day 4 (6.2 false positives±0.86), the number of false positive responses fell to 0.7±0.21; 0.7±0.26 and 1±0.21 for MK 801, 7-CK and gacyclidine respectively (FIG. 5C). Altogether, these results provides evidence salicylate acts on cochlear fast synaptic transmission via the activation of NMDA receptors, accounting for the occurrence of tinnitus

CONCLUSION

From the above experiments It can be concluded that human tinnitus is produced by aberrant glutamate-mediated neurotransmission mediated by NMDA receptors, and that NMDA receptor antagonist may be used to treat such tinnitus. The current disclosure suggests that specific NMDA receptor antagonists block salicylate-induced tinnitus without causing undesired hearing loss associated with suppression of AMPA receptor-mediated signals. Such NMDA antagonists may be include (but are not limited to) D-AP5 (D-2-amino-5-phosphonopentanoate), Dizocilpine (MK 801), 7-chlorokynurenate or Gacyclidine (GK-11). Such treatment includes delivery onto or in the vicinity of the round window niche of the inner ear, for example to the middle-inner membrane or to the annular ligament of the stapes footplate. Analogues and derivatives of such drugs may equally be used.

Having herein described preferred embodiments of the invention, it is anticipated that suitable modifications may be made thereto by individuals skilled in the art, which nonetheless remain within the scope of the invention. For example, the invention shall not be limited with respect to the exemplary compositions used or construction materials being employed. In this regard, the invention shall only be construed in accordance with the following claims:

What is claimed is:

1. A method for treating an inner ear disorder in a subject, the disorder being caused by aberrant glutamate-mediated neurotransmission, the method comprising:
   administering directly to the inner ear of a subject suffering from an inner ear disorder, a formulation comprising an agent, wherein the agent is gacyclidine, thereby treating the inner ear disorder in the subject,
   wherein said administration results in modulation of glutamate-mediated neurotransmission without causing significant clinical hearing loss associated with suppression of AMPA receptor-mediated signals.

2. The method of claim 1, wherein the agent is administered by diffusion across a middle-inner ear membrane.

3. The method of claim 2 wherein the agent is delivered to the round window membrane of the inner ear for a period of at least about 3 days.

4. The method of claim 1, wherein the agent is delivered at a rate of from about 0.1 mg per hour to 200 mg per hour, continually, for a period of at least 24 hours.

5. The method of claim 1, wherein the inner ear disorder comprises tinnitus.

* * * * *